United States Patent [19]

Reynaud

[11] Patent Number: 4,738,616
[45] Date of Patent: Apr. 19, 1988

[54] ASSEMBLY CONSTITUTED BY A DRILL AND A TENON FOR ANCHORING DENTAL PROSTHESIS ADAPTED TO BE FIXED IN THE ROOT OF A TOOTH

[76] Inventor: Marc Reynaud, 23, avenue Plaine Fleurie, 38240 Meylan, France

[21] Appl. No.: 905,782

[22] Filed: Sep. 9, 1986

[30] Foreign Application Priority Data

Sep. 13, 1985 [FR] France ................ 85-13622

[51] Int. Cl.⁴ ............................................. A61C 5/08
[52] U.S. Cl. ..................................... 433/220; 433/165
[58] Field of Search ............... 433/173, 174, 165, 220, 433/221, 102

[56] References Cited

U.S. PATENT DOCUMENTS 4,283,176 8/1981 Vajda ........................... 433/220

FOREIGN PATENT DOCUMENTS 2936690 10/1980 Fed. Rep. of Germany .
80794 5/1963 France .
424086 5/1967 Switzerland .

Primary Examiner—Robert Peshock
Attorney, Agent, or Firm—McAulay, Fields, Fisher, Goldstein & Nissen

[57] ABSTRACT

In an assembly constituted by a drill and a tenon for anchoring a dental prosthesis adapted to be fixed in the root of a tooth the drill has a diameter slightly larger than that of the tenon at all points along its length. The tenon and the drill have similar meridian profiles and each is constituted by two coaxial cylindro-conical parts of large and small diameters respectively, the cylindro-conical part of small diameter comprising a cylindrical part connected to the small base of the conical frustum of the cylindro-conical part of large diameter projecting out of the root of the tooth. The tenon and the drill terminate respectively in their truncated end part of small diameter, of which the angle of taper is selected so as to ensure a wedging of the truncated end part of small diameter of the tenon in the corresponding truncated end part of the drilled hole. Futher the truncated end part of the tenon as a length shorter than that of the drill.

20 Claims, 1 Drawing Sheet

ASSEMBLY CONSTITUTED BY A DRILL AND A TENON FOR ANCHORING DENTAL PROSTHESIS ADAPTED TO BE FIXED IN THE ROOT OF A TOOTH

BACKGROUND OF THE INVENTION

The present invention relates to an assembly constituted by a drill and a tenon for anchoring a dental prosthesis adapted to be fixed in the root of a tooth.

Anchoring tenons are known at the present time which are made in different shapes, namely cylindrical, cylindroconical, conical or stepped conical. Each of these types of tenon has advantages and drawbacks.

In particular, Patent No. FR-E-80794 describes an anchoring tenon constituted by two coaxial cylindroconical parts of different diameters, the cylindro-conical part of smaller diameter itself being extended by a cylindrical end part. Such a tenon is positioned in a hole pierced by means of a drill having a profile identical to that of the tenon but of a slightly larger diameter at all points along the length of the tenon. Once positioned in the hole drilled in the root of a tooth, the cylindrical end part of the tenon stops at a certain distance from the bottom of the hole. Such a tenon presents the drawback that it "floats" relatively in its hole and it tends to move out by itself, when silicon is injected for taking an impression, under the effect of the pressure of this silicon injected by means of a syringe. To ensure a firm hold of the tenon in its hole, it is necessary to place circlips in transverse annular grooves in this tenon, which ensure compensation of the clearance. Consequently, such a tenon has a relatively complex structure and is therefore relatively expensive to manufacture; furthermore, it does not enable a strictly calibrated thickness of the layer of sealing cement interposed between each of the cylindrical parts and the wall of the drilled hole to be obtained.

SUMMARY OF THE INVENTION

It is an object of the present invention to overcome these drawbacks by providing an assembly constituted by a drill and an anchoring tenon of particular shapes, allowing excellent retention of the tenon sealed in the root of a tooth.

To that end, this assembly is constituted by a drill and a tenon for anchoring a dental prosthesis adapted to be fixed in the root of a tooth. The drill has a diameter slightly larger than that of the tenon at all points along its length. The tenon and the drill each have similar meridian profiles and each are constituted by two coaxial cylindroconical parts of large and small diameters respectively. The cylindro-conical part of small diameter comprises a cylindrical part connected to the small base of the conical frustum of the cylindro-conical part of large diameter projecting out of the root of the tooth. The tenon and the drill terminate respectively in their truncated end part of small diameter, of which the angle of taper is selected so as to ensure a wedging of the truncated end part of small diameter of the tenon in the corresponding truncated end part of the drilled hole and the truncated end part of the tenon has a length shorter than that of the drill.

The anchoring tenon according to the invention offers the advantage of having a considerably increased power of retention thanks to the presence of the two cylindrical parts, of large and small diameter respectively, and of ensuring an excellent joint with the prosthesis by the cylindrical part of large diameter projecting from the root. Furthermore, this tenon ensures a film of sealing cement having an optimal thickness of between 20 and 40 micrometers, along the two cylindrical parts whilst a conical tenon perfectly in contact with the walls of the cavity cannot allow this minimum thickness of cement. The truncated end part of the tenon respects the taper of the terminal part of the tooth. The step separating the two cylindro-conical parts is located in the cervical zone where the anatomy of the tooth allows this. Passage towards the step is effected by means of a very open cone without rendering the tooth fragile.

BRIEF DESCRIPTION OF THE DRAWINGS

The invention will be more readily understood on reading the following description with reference to the accompanying drawings, in which.

DESCRIPTION OF THE PREFERRED EMBODIMENTS

Figure 1:
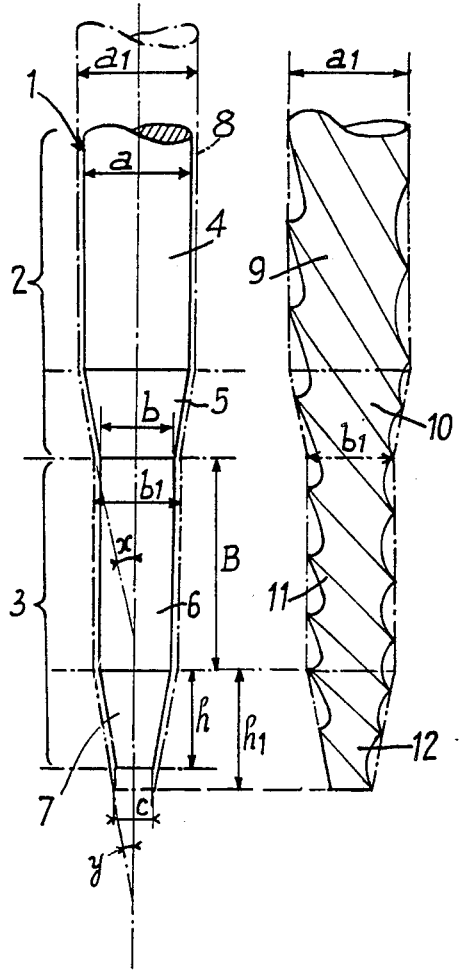
FIG. 1 is a view in elevation of an assembly of a drill and anchoring tenon according to the invention.
Figure 2:
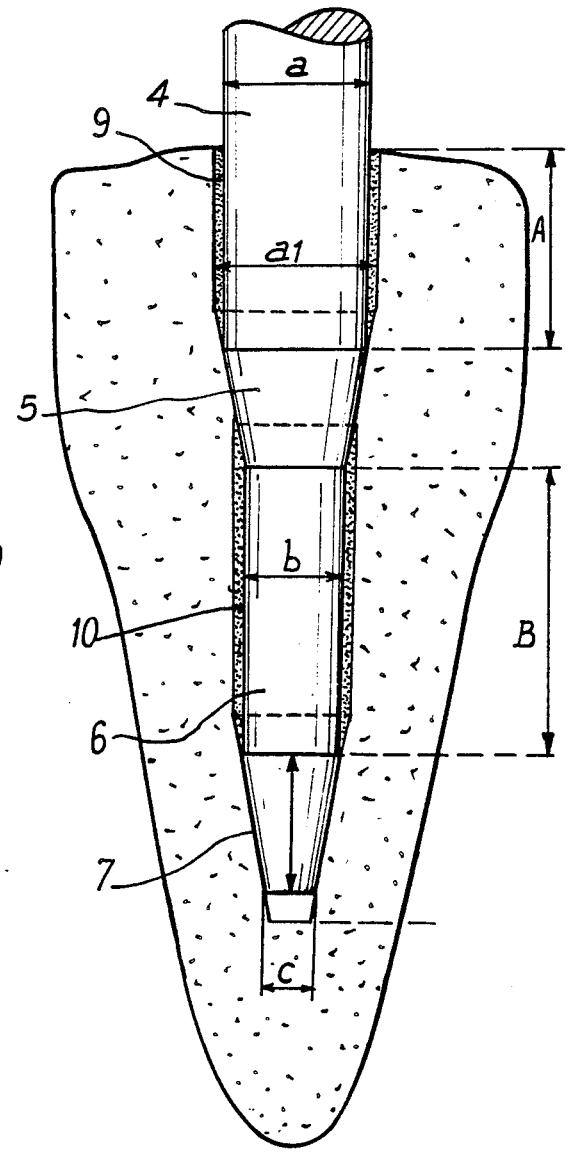
FIG. 2 is a view in axial section of an anchoring tenon according to the invention engaged and sealed in the root of a tooth.

Referring now to the drawings, the anchoring tenon 1 which is shown in FIGS. 1 and 2, is adapted to be engaged and sealed in the root of a tooth, for the purpose of receiving a prosthesis on its outer upper part.

According to the invention, the anchoring tenon 1 is constituted by a single piece of revolution formed by two coaxial cylindro-conical parts in line with each other, namely an upper cylindro-conical part 2, of large diameter and a lower cylindro-conical part 3 of smaller diameter. Cylindro-conical part 2 comprises a cylindrical rod 4 of relatively large diameter a, extended, at its lower end, by a truncated part 5 with small base of diameter b. This small base is followed by a cylindrical rod 6 of diameter b which terminates in a truncated part 7, converging downwardly, and of which the small base has a diameter c.

The taper of the two truncated parts 5 and 7 have different values. More particularly, the end truncated part 7 is sharper (semi-vertex angle y of 6° for example) than the intermediate truncated part 5 (semi-vertex angle x of 11° to 12° for example).

The anchoring tenon 1 is engaged in a hole made in the root of a tooth by means of a drill 8 of which the meridian profile is similar to that of tenon 1 but whose diameter is larger than that of tenon 1, at all points along its length. In other words, drill 8 successively comprises, from top to bottom, an upper cylindrical part 9 of large diameter $a_1$, an intermediate truncated part 10 of semi-vertex angle x, a lower cylindrical part 11 of small diameter $b_1$ and a lower truncated end part 12 of semi-vertex angle y. The larger diameter $a_1$ and small diameter $b_1$ of the drill 8 may be larger than the corresponding diameters a and b of the anchoring tenon 1 by 0.06 mm for example. This is shown in the left-hand part of FIG. 1 where the profile of the drill 8 is shown in chain-dotted lines, superposed on that of tenon 1. The heights of the intermediate truncated parts 5,10 and of the cylindrical parts of small diameter 6,11 are respectively the same for tenon 1 and drill 8, but the truncated end part 12 of drill 8 has a height h1 which is greater than height h of the truncated end part 7 of the anchoring tenon.

When the anchoring tenon 1 is engaged and sealed in the root of a tooth (FIG. 2), its upper cylindrical rod 4 of large diameter a ensures a cylindrical retention, within the root 1, over a distance A of the order of 3 mm. The diameter a of this rod 4 corresponds to the diameter of the junction with the prosthesis and it is reinforced thanks to the provision of the step between the two cylindro-conical parts 2 and 3.

The anchoring tenon according to the invention also ensures a second cylindrical retention over length B corresponding to the length of the cylindrical rod 6 of the cylindro-conical part of small diameter.

The intermediate and end truncated parts 5,7 which are closely engaged in the truncated parts, of corresponding angles of taper, hollowed in the root, ensure a precise centring of the anchoring tenon 1 with respect to the drilled hole. Such precise centring makes it possible to define, about the two cylindrical parts 4 and 6 of the tenon 1, annular spaces 9', 10' for sealing of well-determined width, filled with cement. In this way, each film of cement filling the sealing spaces 9' and 10' has a well-determined thickness, equal to half the difference of the diameters $a_{1-a}$ or $b_{1-b}$ viz. 0.03 mm in the present example. Furthermore, the very sharp truncated end part, i.e. of small semi-vertex angle y, provides a particularly efficient wedging of the tenon 1 in the drilled hole, such wedging opposing the loosening of the tenon from the hole under the effect of the pressure of the material used for impression (silicon), when an impression is taken by injecting silicon under pressure by means of a syringe.

The following Tables gives the values of the dimensions (in mm) of various tenons which have been manufactured and which have given entire satisfaction during the tests carried out:

| diameter a | 1,5 | 1,8 | 2,1 | 2,3 |
|---|---|---|---|---|
| diameter b | 1,1 | 1,2 | 1,4 | 1,5 |
| diameter c | 0,6 | 0,6 | 0,6 | 0,7 |
| height h | 1,5 | 2 | 3 | 2 |
| length B | 2,5 | 3,5 | 4 | 2,5 |

What is claimed is:

1. A system for anchoring a tenon to a tooth to fix a dental prosthesis to the root of the tooth, the system comprising:
   an anchoring tenon having a cylindraceous outer surface and including a prosthesis mounting end, an intermediate section and a root end; and
   a drill to drill the root of the tooth and having a median profile similar to and complementary to said tenon and a diameter larger than said tenon, and wherein said drill includes a unitary member comprising at least one portion corresponding to said prosthesis end, said root end and said intermediate section for drilling an opening into the root of the tooth for receiving said tenon into the root of the tooth to provide an inner receptive area in the root having an inner surface complementary to the outer configuration of said tenon, but having a diametrical extent along the axial length of said tenon greater than the diametrical extent of said tenon for each cross-sectional area thereof; and
   the portion of said drill corresponding to said root end having a frusto-conical configuration with an axial length greater than the axial length of said root end to drill an opening into the root of the tooth having an axial extent greater than the axial length of said root end of said tenon.

2. The system of claim 1, including sealing means inserted between said prosthesis mounting end and the inner wall of the root of the tooth after the tenon has been inserted into the tenon receiving opening in the tooth for sealing the tenon to the root of the tooth.

3. The system of claim 2, wherein said prosthesis mounting end is sealed to the tooth along their common axial extent for 3 mm, by said sealing means.

4. The system of claim 1, wherein the spacing between the tenon and said inner surface is 0.03 mm.

5. The system of claim 1, wherein the diameter of said drill is 0.06 mm greater than the diameter of said cylindraceous member along the axial length thereof.

6. The system of claim 1, wherein said root end is wedged axially into the root portion of the tooth having an inner configuration conforming to the outer configuration of said root end and cooperating with said sealing means to oppose loosening of the tenon from the root under the effect of pressure and to maintain the axis of the root portion coaxial with the axis of the tenon opening in the root portion of the tooth.

7. The system of claim 1, wherein a portion of said intermediate section is wedged into the root portion of the tooth having an inner configuration conforming to the outer configuration of said intermediate part.

8. The system of claim 1, wherein:
   said prosthesis mounting end has a first diameter which is substantially uniform along its entire axial length;
   said intermediate section comprising at least one member having a first part with a second diameter substantially equal to said first diameter and a second part having a third diameter with a diametrical extent less than said first and second diameters; and
   said root end having first and second base portions, said first base portion being free of any connection with said prosthesis mounting end, said first and second base portions having fourth and fifth diameters, respectively, said second base portion having a diameter greater than said first base portion and substantially equal to said third diameter;
   said cylindraceous outer surface of said tenon includes an intermediate part having a substantially uniform cylindrical outer surface along the axial length thereof with a diameter substantially equal to the diameter of the larger base of said root end and having one end connected with said larger base of said root end, and another end connected with said intermediate section; and including:
   sealing means for sealing said intermediate part to the inner wall of the root of the tooth complementary to said intermediate part for holding the tenon in the root of the tooth.

9. The system of claim 8, wherein said sealing means also seals part of said intermediate section to the inner wall of the root portion of the tooth complementary to said intermediate part and seals part of said intermediate part to the inner wall of the root portion complementary to said root end.

10. The system of claim 8, including additional sealing means insterted between said prosthesis mounting end and the inner wall of the root of the tooth for sealing the prosthesis mounting end to the inner wall of the root of the tooth complementary with said prosthesis mounting end and part of said intermediate section and cooperating with said first-mentioned sealing means to together hold the tenon in the root of the tooth.

11. The tenon of claim 1, wherein said intermediate part has a frusto-conical outer configuration.

12. The system of claim 1, wherein the apex angle of said intermediate section is greater than the apex angle of said root end.

13. The system of claim 1, wherein the apex angle of said intermediate part is about 11°–12° and the apex angle of said root end is approximately 6°.

14. A tenon for anchoring a dental prosthesis adapted to be fixed in the root of a tooth, comprising:
- a cylindraceous member including a prosthesis mounting end, an intermediate section and a root end;
- said prosthesis mounting end having a first diameter which is substantially uniform along its entire axial length;
- said root end having a first base portion free of any connection with said prosthesis mounting end and a second base portion associated with said prosthesis mounting end, said root end having a frusto-conical outer shape having second and third diameters, each said diameter being different from each other, said first base portion having a diameter equal to said second diameter and said second base portion having a diameter equal to said third diameter; and
- said intermediate section comprising at least one member having a first part with a fourth diameter equal to said first diameter and a second part having a fifth diameter with a diametrical extent less than said fourth diameter and equal to said third diameter.

15. The tenon of claim 14, wherein said intermediate section has a frusto-conical outer configuration, and the apex angle of said intermediate part is greater than the apex angle of said root end.

16. The tenon of claim 14, wherein the apex angle of said intermediate section is about 11°–12° and the apex angle of said root end is approximately 6°.

17. The tenon of claim 14, wherein said cylindraceous member includes a intermediate part having a substantially uniform cylindrical outer surface along the axial length thereof with a sixth diameter substantially equal to said third and fifth diameters.

18. The tenon of claim 14, said tenon being constituted by a single piece of revolution.

19. The tenon of claim 15, wherein said root end and said intermediate section are differently tapered, and the taper of said root end is sharper than the taper of said intermediate section.

20. A drill for use in a system for anchoring the tenon as claimed in claim 17 to a tooth to fix a dental prosthesis to the root of the tooth, the drill comprising:
- an outer cylindraceous configuration complementary to said tenon;
- said drill having a median profile similar to and complementary to the outer surface portion of said tenon along the axial length thereof and a diameter larger than the diameter of said tenon for all cross-sections thereof;
- at least one section corresponding to said prosthesis end, said root end and said intermediate section for drilling the root of the tooth to provide an inner receptive area in the root complementary to the outer configuration of said tenon, but having a diametrical extent along the axial length of said tenon greater than the diametrical extend of said tenon for each cross-sectional area thereof;
- the portion of said drill corresponding to said root end having a frusto-conical configuration with an axial height greater than the axial height of said root end to drill an opening into the root of the tooth having an axial extent greater than the axial extent of said root end and said intermediate part, but less than the axial extent of said tenon to permit said tenon to fit within said opening but extend thereinto so that the complementary portion of the outer surface of said tenon is displaced from the complementary inner surface of the root of the tooth to provide for a wedging action to take place between the inner surface and the outer surface of the tenon while permitting the insertion of a sealer in the space between the tenon and the root of the tooth.

* * * * *